US005972487A

United States Patent [19]

Duenk et al.

[11] Patent Number: 5,972,487

[45] Date of Patent: Oct. 26, 1999

[54] ABSORBENT STRUCTURES

[75] Inventors: Elisabeth Hendrika Duenk, Brussels, Belgium; Walter Jakob Fischer, Euskirchen-Flamersheim, Germany

[73] Assignee: The Procter & Gamble Company, Cincinnati, Ohio

[21] Appl. No.: 07/091,316

[22] Filed: Aug. 31, 1987

Related U.S. Application Data

[63] Continuation of application No. 06/851,760, Apr. 14, 1986, abandoned.

[30] Foreign Application Priority Data

Apr. 15, 1985 [GB] United Kingdom ................... 8509591

[51] Int. Cl.[6] ........................................ B32B 7/02

[52] U.S. Cl. .......................... 428/218; 428/212; 428/323; 604/367; 604/368

[58] Field of Search .................................... 604/367, 368; 428/212, 218, 323

[56] References Cited

U.S. PATENT DOCUMENTS

| | | | |
|---|---|---|---|
| 1,702,530 | 2/1929 | Williams . | |
| 3,073,309 | 1/1963 | Mosier . | |
| 3,121,427 | 2/1964 | Mosier . | |
| 3,669,103 | 6/1972 | Harper et al. . | |
| 3,670,731 | 6/1972 | Harmon | 604/368 |
| 3,675,654 | 7/1972 | Baker et al. . | |
| 3,888,257 | 6/1975 | Cook et al. . | |
| 3,968,798 | 7/1976 | Hokanson . | |
| 4,102,340 | 7/1978 | Mesek et al. | 604/368 |
| 4,103,062 | 7/1978 | Aberson et al. . | |
| 4,105,033 | 8/1978 | Chatterjee et al. . | |
| 4,145,464 | 3/1979 | McConnell et al. . | |
| 4,186,165 | 1/1980 | Abserson et al. . | |
| 4,219,024 | 8/1980 | Patience et al. . | |
| 4,226,237 | 10/1980 | Levesque . | |
| 4,232,674 | 11/1980 | Melican . | |
| 4,235,237 | 11/1980 | Mesek et al. . | |
| 4,318,408 | 3/1982 | Korpman . | |
| 4,333,462 | 6/1982 | Holtman et al. | 604/368 |
| 4,333,463 | 6/1982 | Holtman | 604/368 |
| 4,333,465 | 6/1982 | Weigner . | |
| 4,340,556 | 7/1982 | Ciencewicki . | |
| 4,364,992 | 12/1982 | Ito et al. . | |
| 4,373,519 | 2/1983 | Errede et al. . | |
| 4,381,782 | 5/1983 | Mazurak et al. . | |
| 4,381,783 | 5/1983 | Elias . | |
| 4,410,324 | 10/1983 | Sabee . | |
| 4,460,642 | 7/1984 | Errede et al. . | |
| 4,500,315 | 2/1985 | Pieniak et al. . | |
| 4,537,590 | 8/1985 | Pieniak et al. . | |
| 4,540,454 | 9/1985 | Pieniak et al. . | |
| 4,551,199 | 11/1985 | Kock et al. . | |
| 4,573,988 | 3/1986 | Pieniak et al. . | |
| 4,578,068 | 3/1986 | Kramer et al. . | |
| 4,604,313 | 8/1986 | McFarland et al. . | |
| 4,610,678 | 9/1986 | Weisman et al. | 604/368 |
| 4,650,479 | 3/1987 | Insley . | |
| 4,654,039 | 3/1987 | Brandt et al. . | |
| 4,655,757 | 4/1987 | McFarland et al. . | |
| 4,657,537 | 4/1987 | Zimmerer . | |
| 4,673,402 | 6/1987 | Weisman et al. . | |
| 4,685,909 | 8/1987 | Berg et al. . | |
| 4,685,915 | 8/1987 | Hasse et al. . | |
| 4,699,823 | 10/1987 | Kellenberger et al. . | |
| 4,715,918 | 12/1987 | Lang . | |

FOREIGN PATENT DOCUMENTS

| | | |
|---|---|---|
| 0108637 | 5/1984 | European Pat. Off. . |
| 0122042 | 10/1984 | European Pat. Off. . |
| 122042 | 10/1984 | European Pat. Off. . |
| 59903 | 1/1984 | Japan . |
| 1406615 | 3/1973 | United Kingdom . |
| 2132897 | 7/1984 | United Kingdom . |
| 2140471 | 11/1984 | United Kingdom . |
| 2145661 | 4/1985 | United Kingdom . |

*Primary Examiner*—James J. Bell
*Attorney, Agent, or Firm*—Steven W. Miller; E. Kelly Linman; Jacobus C. Rasser

[57] ABSTRACT

Absorbent structures comprising a continuous matrix of hydrophilic fibers, having dispersed therein particles of a water-insoluble hydrogel, are disclosed.

37 Claims, No Drawings

ABSORBENT STRUCTURES

This is a continuation of application Ser. No. 851,760, filed on Apr. 14, 1986 aband.

TECHNICAL FIELD

This invention relates to absorbent structures which are used to absorb fluids, especially body fluids and wastes. The absorbent structures herein are employed as the fluid absorbing member in products such as baby diapers, adult incontinence items, bandages, catamenials, bed pads, and the like.

BACKGROUND OF THE INVENTION

Water-insoluble hydrogels have been proposed for use in absorbent structures. A major drawback of the hydrogel materials is their relatively high cost, as compared to conventional absorbent materials like cotton and wood pulp fibers. A second drawback is a phenomenon called gel-blocking: when exposed to a fluid, the outer layers of a hydrogel particle swell, thus preventing fluid to reach the inner layers of the particle other than by a relatively slow diffusion process. Because of this gel blocking, hydrogel materials have relatively poor absorption kinetics.

One general approach towards solving this problem is to provide a multilayer structure, comprising one or more hydrogel containing layers and one or more wicking layers.

Examples of this approach are disclosed in: U.S. Pat. No. 4,364,992, issued Dec. 21, 1982 to Ito et al; U.S. Pat. No. 4,102,340, issued Jul. 25, 1978 to Mesek et al; and in EP-PA 83306764.8, publication No. 0 108 637.

A drawback of this approach is that the wicking layer does not have the excellent rewet properties of hydrogel material. Another drawback is the relatively high manufacturing cost of multilayer structures.

EP PA 8430 1578.5, publication No., 0 122 042, discloses absorbent structures comprised of a hydrophilic fibrous matrix having dispersed therein discrete particles of a water-insoluble hydrogel material. The structures are compressed to a relatively high density, so as to ensure good wicking.

Although this latter approach provides absorbent structures having a good performance in terms of rewet and absorbent capacity, there is still room for improvement. The high cost of hydrogel materials make a further increase of the absorbent capacity per gram of material highly desirable.

It is therefore an object of the present invention to provide a hydrogel-comprising absorbent structure having an improved absorbent capacity per gram of hydrogel material used.

SUMMARY OF THE INVENTION

The present invention relates to absorbent structures having a top face and back face, and comprising a continuous matrix of hydrophilic fibers having dispersed therein discrete particles of a water-insoluble hydrogel, characterized in that the back face half of the absorbent structure contains at least 60% of the water-insoluble hydrogel material.

DETAILED DESCRIPTION OF THE INVENTION

This invention relates to absorbent structures comprising hydrogel particles dispersed in a continuous matrix of hydrophilic fibers. The basis of this invention is the discovery that the absorbent capacity of such structures can be increased by preferentially placing the hydrogel particles near the face of the structure which is turned away from the point of fluid discharge.

Absorbent structures intended for use in e.g., diapers or catamenials typically have a more or less planar configuration. For convenience, the face of the structure intended to be placed nearest to the body of the person using it will be referred to herein as the "top face". The opposing face will be referred to as the "back face". The absorbent structures herein comprise a continuous matrix of hydrophilic fibers having dispersed therein discrete particles of a water-insoluble hydrogel. The distribution of hydrogel particles is skewed towards the back face of the structure. If the structures herein were to be cut into two halves along a plane substantially parallel to the top face and the back face, the resulting back face half would contain at least 60% of the total amount of hydrogel material, whereas the top face half would contain not more than 40% of the total amount. Preferably, the back face half contains at least 70% of the total amount of hydrogel, most preferably from 75% to 100%. The hydrogel distribution in any given plane substantially parallel to the top face and back face can be homogenous or nonhomogenous.

Any hydrogel distribution resulting in 60% or more of the hydrogel to be dispersed in the back face half of the structure are suitable for the puposes of the present invention.

Examples of such hydrogel distributions include structures which, in the Z-direction (from top face to bottom face) comprise an area of, e.g., 1–3 mm of low hydrogel concentration, followed by a gradually increasing hydrogel concentration. Instead of a gradual increase of hydrogel concentration, there can be a rather abrupt increase.

Highly preferred are structures having, immediately adjacent to the back face, a thin (e.g., 0.5–2 mm) area of low (e.g., less than 10%, preferably less than 5%) hydrogel concentration. Structures of this type minimize the risk of hydrogel particles perforating the backsheet material of articles (diapers, catamenials, etc) in which the structures are used. Moreover, this area of low hydrogel concentration acts as a wicking layer.

By "hydrogel" as used herein is meant an inorganic or organic compound capable of absorbing aqueous fluids and retaining them under moderate pressures. For good results, the hydrogels must be water insoluble. Examples are inorganic materials such as silica gels and organic compounds such as cross-linked polymers. Cross-linking may be a covalent, ionic, vander Waals, or hydrogen bonding. Examples of polymers include polyacrylamides, polyvinyl, alcohol, ethylene/maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogels are those disclosed in U.S. Pat. No. 3,901,236, issued to Assarsson et al. Aug. 26, 1975, the disclosures of which are incorporated herein by reference. Particularly preferred polymers for use herein are hydrolyzed acrylonitrile grafted starch, arcylic acid grafted starch, polyacrylates, and isobutylene/maleic anhydride copolymers, or mixtures thereof.

Processes for preparing hydrogels are disclosed in U.S. Pat. No. 4,076,663, issued Feb. 28, 1978 to Fusayoshi Masuda et al.; in U.S. Pat. No. 4,286,082, issued Aug. 25, 1981 to Tsuno Tsubakimoto et al.; and further in U.S. Pat. Nos. 3,734,876, 3,661,815, 3,670,731, 3,664,343, 3,783, 871, and Belgian Patent 785,858; the disclosures of all of which are incorporated herein by reference.

As used herein "Particles" include particles of any shape, e.g. spherical or semi-spherical, cubic, rod-like, polyhedral, etc.; but also shapes having a large greatest dimension/smallest dimension ratio, like needles, flakes and fibers, are contemplated for used herein. By "particle size" as used herein is meant the weight average of the smallest dimension of the individual particles. Conglomerates of hydrogel particles may also be used, provided the weight average size of such conglomerates is within the limits set forth hereinbelow.

Although the absorbent structures of the present invention are expected to perform well with hydrogel particles having a particles size varying over a wide range, other considerations may preclude the use of very small or very large particles. For reasons of industrial hygiene, (weight) average particle sizes smaller than about 30 micrometers are less desirable. Particles having a smallest dimension larger than about 4 mm may cause a feeling of grittiness in the absorbent structure, which is undesirable from a consumer standpoint. Preferred for use herein are particles having an (weight) average particle size of from about 50 micrometers to about 1 mm.

The type of hydrophilic fibers is not critical for use in the present invention. Any type of hydrophilic fiber which is suitable for use in conventional absorbent products is also suitable for use in the absorbent structure of the present invention. Specific examples include cellulose fibers, rayon, polyester fibers. Other examples of suitable hydrophilic fibers are hydrophilized hydrophobic fibers, like surfactant-treated or silica-treated thermoplastic fibers. Also, fibers which do not provide webs of sufficient absorbent capacity to be useful in conventional absorbent structures, but which do provide good wicking properties, are suitable for use in the absorbent structures of the present invention. This is so because, for the purposes of the present invention wicking properties of the fibers are far more important than their absorbent capacity. For reasons of availability and cost, cellulose fibers, in particular wood pulp fibers, are preferred.

Preferred are absorbent structures which contain from 3% to 40%, by total dry weight of the structure, of the hydrogel material. More preferred are structures containing from 8% to 20% of hydrogel material.

Since the fibrous matrix and the hydrogel particles are chemically different, the hydrogel distribution can be verified by chemical analysis, using well established chemical techniques. Typically, representative samples are taken from the top face half and and the back face half, respectively, of the absorbent structures. The samples are then analyzed for hydrogel content. The hydrogel content of the back face half sample should be at least 1.5 times the hydrogel content of the sample taken from the top face half of the structure.

As an example, a structure containing 15% hydrogel material (by total dry weight of the structure), 80% of which is disposed in the back face half of the structure, has a hydrogel content as follows:

$$\text{back face half: } \frac{0.8 \times 0.15}{0.5} \times 100\% = 24\%$$

$$\text{top face half: } \frac{0.2 \times 0.15}{0.5} \times 100\% = 6\%$$

the back face half containing four times as much hydrogel as the top face half.

Since many of the commercially available hydrogel materials contain acid (carboxylic, sulfonic, etc) groups, an acid-base indicater can be used for a semi-quantitative determination of the hydrogel distribution.

For example, a crosslinked polyacrylate hydrogel has carboxy radicals as its functional groups. These carboxy groups are predominantly in the salt (e.g., sodium) form. The acid-base indicator bromocresol purple (5', 5"-dibromo-O-cresolsulfone phtalein; yellow-pH 5.2 to 6.8-purple) turns to its alkaline (purple) color when contacted with a polyacrylate hydrogel.

The distribution of a polycarboxylate hydrogel in an absorbent structure can be made visible as follows: 50 mg bromocresol purple is dissolved in 1 liter distilled water. The pH of the solution is adjusted to 5, using HC1. 400 ml of the yellow solution are poured evenly onto the absorbent structure to be tested.

The solution is allowed to penetrate for about two minutes. The intensity of the purple color is a measure of the amount of hydrogel present. The hydrogel distribution can be studied by comparing the color intensities at the top face and the back face of the absorbent structure.

In an alternate procedure, the structure is cut in the Z-direction (=from top face to back face) when still in the dry condition. After application of the indicator solution, the hydrogel distribution in the Z-direction can be estimated.

The assembly of baby diapers, catamenials and the like, using the herein-described absorbent structures, employs various liquid permeable topsheet materials, liquid impermeable backsheet materials, leg bands, tape fasteners and the like, all of which are described in the patent literature. See U.S. Pat. Nos. 3,848,594 (tape fasteners); 3,860,003 (diaper construction); 4,081,301 (attachment of leg elastics); 3,929,135, 4,041,951 and 4,342,314 (improvements in topsheets) for thorough instructions regarding the assembly of diapers, catamenials, and the like.

The manufacture of absorbent mats, especially "air-felt", is well-known and involves using an air stream to conduct fibrous material (e.g. cellulose) into a concave template of any desired depth and shape. The depth of the template determines the thickness of the resulting mat. Moisture or urine-impervious resins may be used to hold the mat in shape and the mat may be compressed to any desired Taber stiffness; see U.S. Pat. No. 3,860,003, cited above.

The following Example illustrates a preferred diaper made according to the present invention. The dimensions listed in the Example are for a diaper intended for use with a child in the 6 to 10 kilogram size range. These dimensions can be modified proportionately for different size children, or for adult incontinence briefs, according to standard commercial practice. As is well-known in the art, such diapers will comprise: a backsheet (the sheet used outermost from the skin, and which is generally made from urine-impenetrable plastic material to give the containment effect of plastic pants); an absorbent structure that will absorb and help contain urine and/or fecal matter; and, generally, a topsheet (the sheet closest to the skin) that is urine-permeable.

While materials used in the assembly of disposable diapers and the like are well-known, the following may be mentioned, solely by way of example.

Backsheet: The backsheet can comprise a urine-impervious polymer sheet, for example polyethylene or polypropylene, that is thin enough to be flexible. A polyethylene sheet 0.01–2 mm thick is typical.

Topsheet: The diaper topsheet can comprise any loosely-woven or nonwoven cloth or scrim-type material that is urine-porous and comfortable to the skin. A nonwoven sheet comprising polypropylene fibres is typical.

Elastic Members: The elastic used to provide leg gathers in the diapers can comprise elastic bands or threads, or elastic adhesive applied as a band or ribbon. One or more elastics can be applied longitudinally along both sides of the diaper, and laid-down either on the topsheet, on the backsheet, or sandwiched between said sheets. In a typical mode, the elastic is pre-stretched, then glued to the diaper using an elastic adhesive, all in well-known fashion. (see U.S. Pat. No. 4,081,301).

Fasteners: The diapers can be fastened by any convenient means, such as pins, snaps and the like. Typical fasteners comprise adhesive tapes, especially tapes in the "Y"configuration described in the patent literature.

Assembly Means: The diapers herein can be assembled by any convenient bonding means, such as heat-sealing, ultrasonic sealing, and the like. Typically, urine-stable adhesives are used to assemble disposable diapers.

Assembly Methods and Apparatus: The apparatus used to form the diapers herein constitutes no part of the present invention. Indeed, such articles may be assembled by hand.

EXAMPLE I

In a conventional air-laying method, absorbent structures are formed by air-conveying a mass of dry wood pulp fibers onto a rotating wire mesh drum. A pressure gradient is maintained over the wire mesh to ensure proper deposition of the fluff.

The structures of the present invention can be made by metering hydrogel particles into the wood pulp fiber stream. Metering can be done by means of e.g., a weighing belt or a screw pump.

Feeding of the hydrogel particles onto the laydown drum can be by gravity or forced air feed.

In either case, a nozzle is used to spread the hydrogel particles over the crotch-width of the absorbent structure.

Since the lay-down drum rotates while wood pulp fibers are being deposited onto it, the position of the hydrogel feed nozzle with respect to the drum and the wood pulp infeed largely determines the distribution of the hydrogel particles in the structure.

The face of the structure which is in contact with the drum will become the back face. Seen from a vantage point from which the drum appears to have a clock-wise rotation, the left hand part of the wood pulp stream reaches the drum first. By placing the hydrogel in a way as to ensure predominant mixing with this left hand part of the wood pulp stream, the desired hydrogel distribution is obtained.

Absorbent structures were made, comprised of wood pulp fibers ("airfelt") and particulate crosslinked polyacrylate hydrogel. The structures had a target weight of 43.58 g, 14% of which was hydrogel, and 85.1% of which was airfelt. The structures were calendered to a thickness of about 6.5 mm.

The hydrogel distribution was determined, using the bromocresol purple indicator method described hereinabove.

Structures made with gravity feed of the hydrogel had the following distribution (Z-direction, going from top face to back face).

| | |
|---|---|
| Top 1–2 mm: hydrogel/airfelt ratio | 0/100–10/90 |
| next 4–5 mm: hydrogel/airfelt ratio | 20/80–50/50 |
| back face 0.5 mm: hydrogel/airfelt ratio | 0/100–10/90 |

Based on the above estimates, the back face half of the structure was calculated to contain 67% of the total amount of hydrogel material. Having a thin area of low hydrogel concentration immediately adjacent to the back face, this structure is an example of the highly preferred structures herein.

Structures made with forced air feed had the following hydrogel distribution (Z-direction, from top face to back face).

Top 4–5 mm: hydrogel/airfelt ratio 0/100–5/95 Back 1.5–2.5 mm: hydrogel/airfelt ratio 50/50.

Based on these estimates, the back face half of the structure was calculated to contain at least 85% of the total amount of hydrogel material.

Both structures, when incorporated in an otherwise conventional diaper, had improved leakage performance and wicking performance as compared to homogenous hydrogel/airfelt blend structures containing the same amounts of hydrogel and airfelt.

EXAMPLE II

A diaper is assembled from the following materials.

1. Backsheet: 0.025–0.070 mm polyethylene: width at top and bottom 33 cm; notched inwardly on both sides to a width-at-center of 28.5 cm; length 50.2 cm.

2. Topsheet: spun-bonded polypropylene, basis weight 21.5g/m$^2$–24.5g/m$^2$; width at top and bottom 33 cm; notched inwardly on both sides to a width-at-center of 28.5 cm; length 50.2 cm.

3. Absorbent structure: prepared in the manner of Example I;, Taber range 7–9.5; 8.4 mm thick, calendered; width at top and bottom 28.6 cm; notched inwardly at both sides to a width-at-center of 10.2 cm; length 44.5 cm.

4. Elastics: four individual rubber strips (2 per side); width 4.77 mm; length 370 mm; thickness 0.178 mm (all the foregoing dimensions being in the relaxed state.)

The diaper of Example II is assembled by overlaying the topsheet on the top face of said absorbent structure; overlaying the backsheet over the back face of said absorbent structure; and gluing the assembly together with urine-stable adhesive.

The elastic bands (designated "inner" and "outer", corresponding to the bands closest to, and farthest from, the core, respectively) are stretched to ca. 50.2 cm and positioned between the topsheet:backsheet along each longitudinal side (2-bands per side) of the core. The inner bands along each side are positioned ca. 55 mm from the narrowest width of the core (measured from the inner edge of the elastic band). The bands are affixed with glue.

The tape functions are affixed to the assembled diaper, which is then ready for use.

What is claimed is:

1. An absorbent structure having a top face, a back face, a top face half, and a back face half and comprising a continuous matrix of hydrophilic fibers having dispersed therein in both said top face half and said back face half discrete particles of a water-insoluble hydrogel, characterized in that the hydrogel content of said back face half of the absorbent structure contains at least 1.5 times the hydrogel content of said top face half of the absorbent structure so that at least 60% of the water-insoluble hydrogel material is contained within said back face half.

2. An absorbent structure according to claim 1 comprising from 3% to 40%, by dry weight of the structure, of water-insoluble hydrogel.

3. An absorbent structure according to claim 1 wherein the water-insoluble hydrogel is selected from the group consisting of hydrolyzed acrylonitrile grafted starch, acrylic acid grafted starch, polyacrylates, copolymers of isobutylene and maleic anhydride, and mixtures thereof.

4. An absorbent structure according to claim 1 wherein the hydrogel particles have an average particle size of from 30 micrometer to 4 mm.

5. An absorbent structure according to claim 1 wherein the hydrophilic fibers are cellulosic fibers, preferably wood pulp fibers.

6. An absorbent structure according to claim 1 wherein the back face half contains at least 70% of the water-insoluble hydrogel material.

7. An absorbent structure according to claim 1 comprising from 8% to 20%, by weight of the structure, of water-insoluble hydrogel.

8. An absorbent structure according to claim 1 having a thin area of low hydrogel concentration immediately adjacent to the back face.

9. An absorbent structure according to claim 1 wherein the hydrogel content of said back face half of the absorbent structure contains at least 4 times the hydrogel content of said top face half of the absorbent structure so that at least 80% of the water-insoluble hydrogel material is contained within said back face half.

10. An absorbent structure according to claim 9 wherein said back face half contains at least 85% of the water-insoluble hydrogel material.

11. An absorbent structure according to claim 10 wherein said top face half contains a hydrogel/airfelt ratio of less than about 5/95.

12. An absorbent structure according to claim 10 comprising from 3% to 40%, by dry weight of the structure, of water-insoluble hydrogel.

13. An absorbent structure according to claim 12 wherein the water-insoluble hydrogel is selected from the group consisting of hydrolized acrylonitrile grafted starch, acrylic acid grafted starch, polyacrylates, copolymers of isobutylene and maleic anhydride, and mixtures thereof.

14. An absorbent structure according to claim 13 wherein the hydrophilic fibers are cellulosic fibers, preferably wood pulp fibers.

15. An absorbent structure according to claim 14 wherein the hydrogel particles have an average particle size of from 30 micrometer to 4 mm.

16. An absorbent structure according to claim 15 comprising from 8% to 20%, by weight of the structure, of water-insoluble hydrogel.

17. An absorbent structure according to claim 16 wherein said hydrogel distribution in any given plane substantially parallel to said top face and said back face is homogenous.

18. An absorbent structure according to claim 1 having an area of low hydrogel concentration immediately adjacent to said front face.

19. An absorbent structure according to claim 18 wherein said hydrogel/airfelt ratio is between about 0/100 to about 10/90.

20. An absorbent structure according to claim 19 wherein said area of low hydrogel concentration is followed by a gradually increasing hydrogel concentration.

21. An absorbent structure according to claim 18 additionally comprising an area of low hydrogel concentration immediately adjacent to said back face.

22. An absorbent article according to claim 21 wherein the hydrogel/airfelt ratio of both areas of low hydrogel concentration are between 0/100 and about 10/90.

23. An absorbent article according to claim 22 wherein said area of low hydrogel concentration adjacent said top face is followed by a gradually increasing hydrogel concentration.

24. An absorbent structure according to claim 23 wherein said back face half contains 67% of the water-insoluble hydrogel material.

25. An absorbent article according to claim 22 comprising from 3% to 40%, by dry weight of the structure, of water-insoluble hydrogel.

26. An absorbent structure according to claim 25 wherein the water-insoluble hydrogel is selected from the group consisting of hydrolized acrylonitrile grafted starch, acrylic acid grafted starch, polyacrylates, copolymers of isobutylene and maleic anhydride, and mixtures thereof.

27. An absorbent structure according to claim 26 wherein the hydrophilic fibers are cellulosic fibers, preferably wood pulp fibers.

28. An absorbent structure according to claim 27 wherein the hydrogel particles have an average particle size of from 30 micrometer to 4 mm.

29. An absorbent article according to claim 28 comprising from 8% to 20%, by weight of the structure, of water-insoluble hydrogel material.

30. An absorbent structure according to claim 1 wherein the hydrogel distribution in any given plane substantially parallel to said top face and said back face is homogenous.

31. A disposable diaper or catamenial product comprising:

(a) a liquid impervious backing sheet;

(b) a hydrophobic, liquid pervious top sheet; and (c) an absorbent structure according to claims 1, 8, 10, 17, 18, 23, 26 or 30 wherein the backing sheet overlays the back face of the absorbent structure and the top sheet overlays the top face of the absorbent structure.

32. An absorbent structure having a top face and a back face and comprising a continuous matrix of hydrophilic fibers having dispersed therein discrete particles of a water-insoluble hydrogel, characterized in that the hydrogel concentration gradually increases from said top face to said back face so that the distribution of hydrogel particles is skewed towards said back face of the absorbent structure.

33. The absorbent structure according to claim 32 wherein the hydrogel distribution in any given plane substantially parallel to said top face and said back face is homogenous.

34. The absorbent structure according to claim 33 additionally comprising an area of low hydrogel concentration adjacent to said front face and an area of low hydrogel concentration adjacent to said back face.

35. An absorbent structure according to claim 34 wherein said areas of low hydrogel concentration have a hydrogel concentration less than about 10%.

36. An absorbent structure according to claim 34 wherein said areas of low hydrogel concentration have a hydrogel concentration less than about 5%.

37. An absorbent structure according to claim 36 wherein the hydrogel particles have an average particle size of from 30 micrometer to 4 mm.

* * * * *